United States Patent
Samson

(10) Patent No.: US 11,324,643 B1
(45) Date of Patent: May 10, 2022

(54) REUSABLE TAMPON APPLICATOR

(71) Applicant: Jessica Samson, Santa Monica, CA (US)

(72) Inventor: Jessica Samson, Santa Monica, CA (US)

( * ) Notice: Subject to any disclaimer, the term of this patent is extended or adjusted under 35 U.S.C. 154(b) by 0 days.

(21) Appl. No.: 16/918,956

(22) Filed: Jul. 1, 2020

Related U.S. Application Data

(60) Provisional application No. 62/869,340, filed on Jul. 1, 2019.

(51) Int. Cl.
*A61F 13/26* (2006.01)

(52) U.S. Cl.
CPC .................... *A61F 13/266* (2013.01)

(58) Field of Classification Search
CPC ................................................ A61F 13/26–266
See application file for complete search history.

(56) References Cited

U.S. PATENT DOCUMENTS

| | | | | |
|---|---|---|---|---|
| 4,148,317 | A * | 4/1979 | Loyer | A61F 13/263 604/11 |
| 9,532,907 | B1 * | 1/2017 | Agrawal | A61F 13/2097 |
| 2005/0197615 | A1 * | 9/2005 | Gann | A61F 13/26 604/11 |
| 2006/0213918 | A1 * | 9/2006 | Rajala | A61F 13/26 221/33 |
| 2007/0204754 | A1 * | 9/2007 | Hook | A61F 13/2082 101/6 |
| 2010/0324468 | A1 * | 12/2010 | Gann | A61F 13/266 604/15 |
| 2019/0350767 | A1 * | 11/2019 | Kight | A61F 13/26 |
| 2020/0330288 | A1 * | 10/2020 | Duensing | A61F 13/2045 |

FOREIGN PATENT DOCUMENTS

| EP | 3827797 A1 * | 6/2021 | ........... A61F 13/266 |
|---|---|---|---|
| ES | 1217271 U * | 9/2018 | ........... A61F 13/266 |

* cited by examiner

*Primary Examiner* — Susan S Su
(74) *Attorney, Agent, or Firm* — Eric Karich; Karich & Associates

(57) ABSTRACT

A tampon applicator has a barrel and a plunger. The barrel extends from a proximal end to a distal end, the distal end having a base opening, and the proximal end having an upper opening exposing an inner chamber. A window formed in the barrel is shaped to receive a tampon. A set of protrusions extends inwardly from the inner chamber proximate the distal end of the barrel, and an inner ring of the inner chamber is proximate the distal end of the barrel. The plunger extends from a first end to a second end, the first end having a base. A top ring is on the base of the plunger, wherein the inner ring of the barrel is adapted to removably snap into the top ring. A annular ridge is on the second end of the plunger for threaded engagement with the set of protrusions of the barrel.

5 Claims, 2 Drawing Sheets

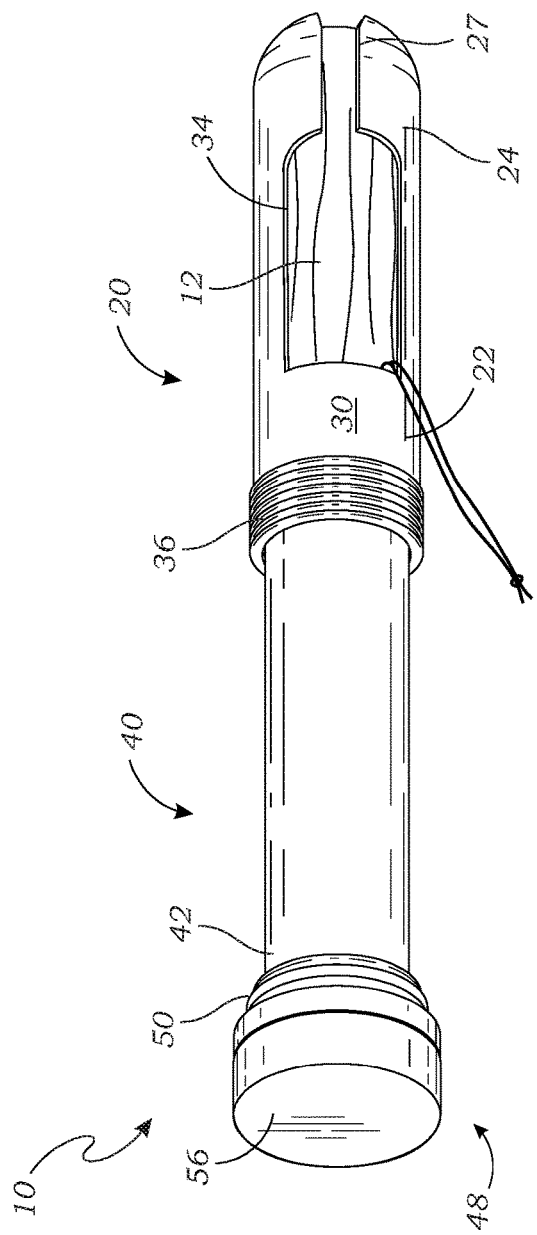
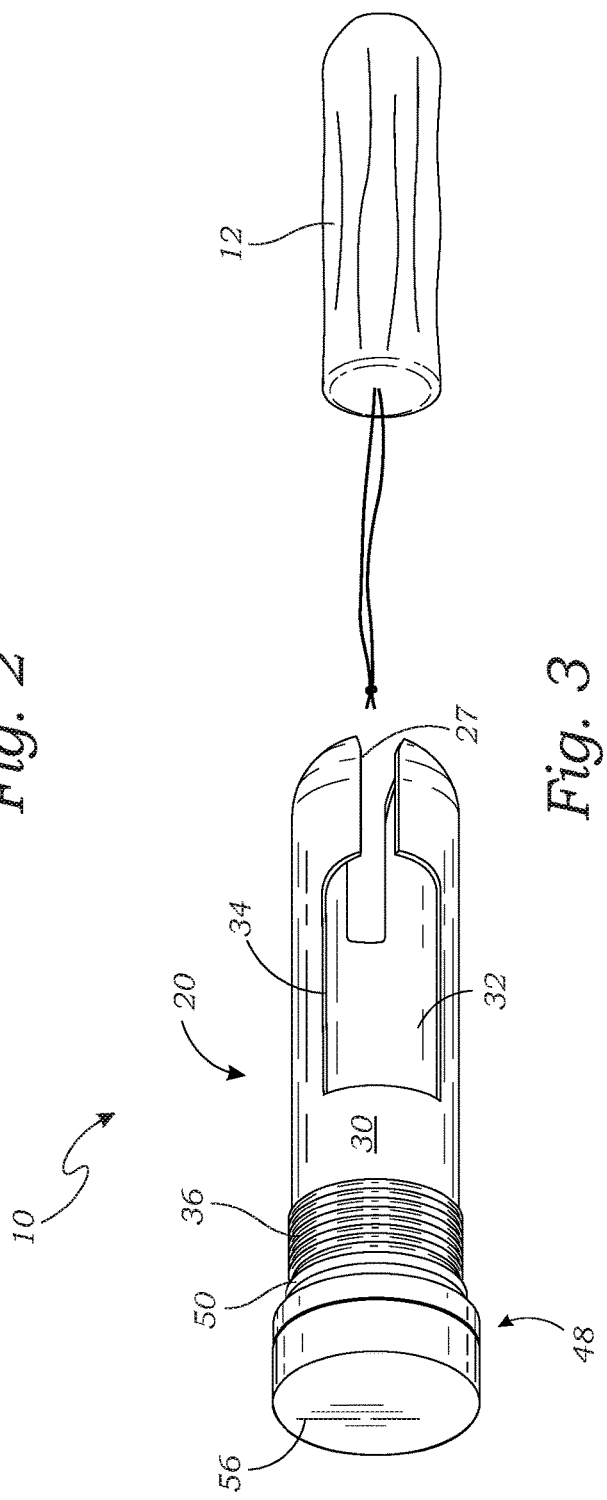

REUSABLE TAMPON APPLICATOR

CROSS-REFERENCE TO RELATED APPLICATIONS

This application for a utility patent claims the benefit of U.S. Provisional Application No. 62/869,340, filed Jul. 1, 2019.

BACKGROUND OF THE INVENTION

Field of the Invention

This invention relates generally to female sanitary products, and more particularly to a reusable tampon applicator.

Description of Related Art

The prior art teaches a variety of tampon applicators which are known in the art. Examples of prior art applicators include the following:

Agrawal, U.S. Pat. No. 9,532,907 (assigned to Thinx, Inc.), teaches a reusable tampon applicator that is adapted for sustainable, environmentally friendly use. This applicator includes a two-part construction that includes a plunger, and a barrel shaped for receiving a tampon. The barrel includes a slot in the side. In use, the barrel is separated from the plunger, and the tampon is inserted into the barrel from the bottom. The plunger is then inserted into the barrel and used for ejecting the tampon. The barrel is made of medical grade silicone, for multiple uses, and includes a slit that extends the entire length of the cylindrical body, and around a top end, and towards the distal end on the other side to form a partial slot on a second lateral side. This forms two halves which can separate to allow ejection of the tampon.

Lemay, U.S. Pat. No. 9,737,443 (assigned to Edgewell), teaches a tampon applicator that includes a barrel having an insertion tip at a forward end of the barrel, a main body section that extends from the insertion tip, and a reverse taper section that is joined to the main body section so that the main body section is between the insertion tip and the reverse taper section. The main body section tapers toward the insertion tip section. The reverse taper section tapers in a direction away from the insertion tip section. A finger grip section extends from the reverse taper section to a plunger receiving end of the barrel opposite the forward end. The barrel is straight from the forward end to the plunger receiving end that receives a plunger. Similar products are shown in Buell, U.S. Pat. No. 9,427,361 (assigned to Eveready), and Morrow, U.S. Pat. No. 7,963,934.

SUMMARY OF THE INVENTION

The present invention teaches certain benefits in construction and use which give rise to the objectives described below.

The present invention provides a tampon applicator that includes a barrel and a plunger. The barrel extends from a proximal end to a distal end, the distal end having a base opening, and the proximal end having an upper opening exposing an inner chamber. The barrel further has a window formed in the barrel shaped to receive a tampon, a set of protrusions extending inwardly from the inner chamber proximate the distal end of the barrel, and a inner ring of the inner chamber proximate the distal end of the barrel. The plunger extends from a first end to a second end, the first end having a base. A top ring is on the base of the plunger, wherein the inner ring of the barrel is adapted to removably snap into the top ring. A annular ridge is on the second end of the plunger for threaded engagement with the set of protrusions of the barrel.

A primary objective of the present invention is to provide a tampon applicator having advantages not taught by the prior art.

Another objective is to provide a tampon applicator that is reusable to reduce consumer waste from the use of disposable tampon applicators.

Another objective is to provide an applicator that may be used to store a digital tampon prior to use.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 2 is a perspective view of the tampon applicator once it has been assembled and configured into a first position, illustrating the tampon applicator once a digital tampon has been inserted into the tampon applicator for use; and FIG. 3 is a perspective view illustrating the tampon applicator of FIG. 2 once the tampon applicator has been moved to a second position, thereby dispensing the tampon.

DETAILED DESCRIPTION OF THE INVENTION

Figure 1:
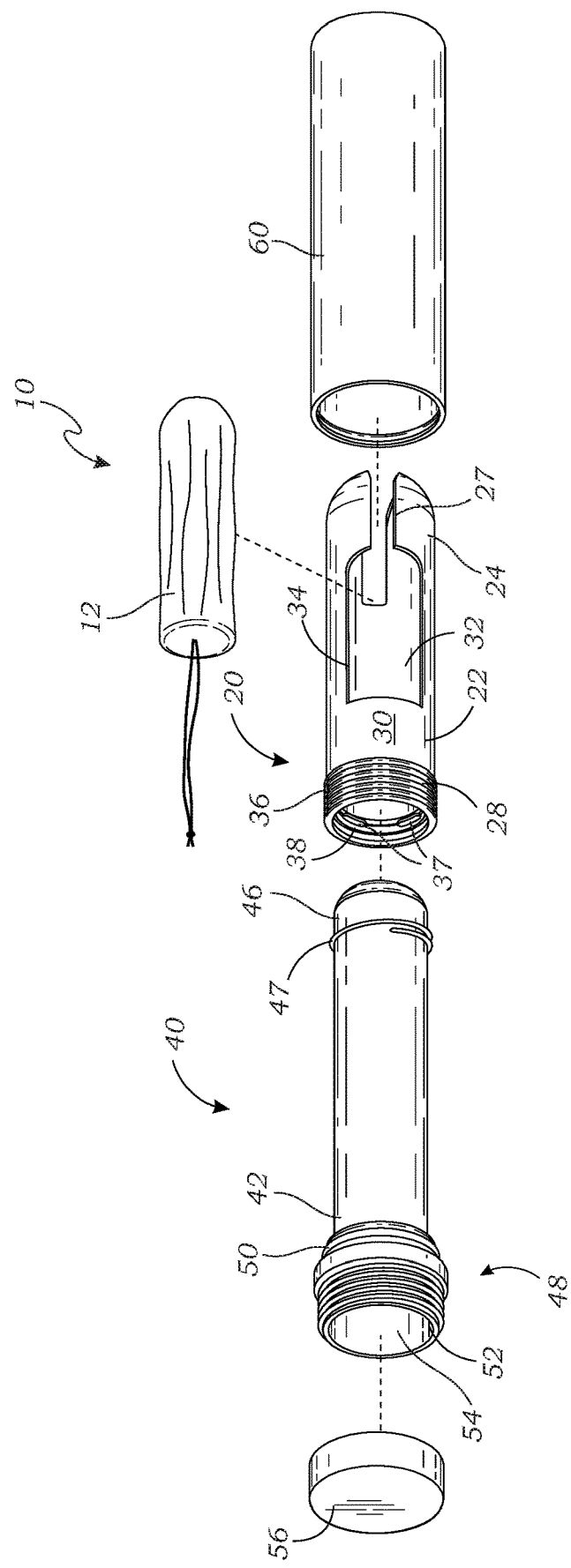
FIG. 1 is an exploded perspective view of a tampon applicator, according to one embodiment of the present invention.

The above-described drawing figures illustrate the invention, a tampon applicator 10 which is adapted for inserting a tampon 12. The applicator 10 may be reusable for reducing consumer waste. The tampon applicator 10 also may be adapted to receive the tampon 12 within a closed compartment for the hygienic storage of the tampon 12, discussed in greater detail below.

FIG. 1 is an exploded perspective view of the tampon applicator 10, according to one embodiment of the present invention. As shown in FIG. 1, in this embodiment the applicator 10 comprises a barrel 20 that is shaped to telescopically receive a plunger 40. In this embodiment, the barrel 20 has a tubular (in this case cylindrical) construction that extends from a proximal end 24 to a distal end 22. The distal end 22 has a base opening 28, and the proximal end 24 has an upper opening 27 exposing an inner chamber 32. In this embodiment, the upper opening 27 of the barrel 20 tapers at least partway down either side of the barrel 20, although this may not be required in alternative embodiments. In some embodiments, the upper opening 27 may be formed to maximize flexibility, e.g., made thinner than the rest of the components of the applicator 10, and/or made of materials that are suitably pliant, or using any other method to ensure pliability, as is known in the art. In other embodiments, the upper opening 27 is constructed of the same material as the rest of the barrel 20 of the applicator 10. In this manner, sections or petals of the upper opening 27 may hold the tampon 12 in place, as described below, yet open under pressure to allow the tampon 12 to be ejected.

The barrel 20 further comprises an outer surface 30 having a window 34 which exposes the inner chamber 32 for insertion of the tampon 12 into the inner chamber 32, best shown in FIG. 2 and described below. As shown in FIG. 1, the outer surface 30 of the barrel 20 at the distal end 22 may be contoured to provide a grip portion 36 that is readily grasped by the user, while manipulating the plunger 40. A set of protrusions 37 may extend inwardly from the inner chamber 32 proximate the distal end 22 of the barrel 20, adjacent an inner ring 38. As shown in FIG. 1, in this embodiment, the set of protrusions 37 of the barrel include four generally equidistant protrusions. The inner ring 38 and the set of protrusions 37 are adapted to engage with a top ring 50 and an annular ridge 47 of the plunger 40, respectively, best shown in FIGS. 2-3 and discussed below.

As shown in FIG. 1, the plunger 40 is an elongate construction that, in this embodiment, is a tubular construction, extending from a first end 42 to a second end 46. The first end 42 includes a base 48, which may be in the form of a raised platform and includes the top ring 50, wherein the inner ring 48 of the barrel 20 are adapted to removably snap into the top ring 50, shown in FIG. 3. In this embodiment, the base 48 of the plunger 40 has a lower opening 52 which exposes a storage compartment 54 within the plunger 40, the lower opening 52 being covered by a removable lid 56. The storage compartment 54 may be used for storing the tampon 12 prior to use. The second end 46 of the plunger 40 is shaped to abut the tampon 12 for pushing the tampon 12, and further includes the annular ridge 47 for threaded engagement with the set of protrusions 37 of the barrel 20, shown in FIG. 2.

In this embodiment, and shown in FIG. 1, the applicator 10 also includes a cap 60, which engages the base 48 of the plunger 40 to lock the cap 60 in place to cover and protect the rest of the applicator 10. In this embodiment, the cap 60 frictionally engages with the plunger 40, clicking in place, but in other embodiments, it may be threadedly engaged, or may be secured onto the plunger 40 using any other mechanism known in the art. In this embodiment, the removable lid 56 of the base 48 is threadedly engaged, but in other embodiments, it may engage in other manners known in the art (e.g., snap or otherwise frictionally engage the base 48, or engage using other mechanisms known in the art).

FIG. 2 is a perspective view of the tampon applicator 10 once it has been assembled and configured into a first position, illustrating the tampon applicator 10 once the digital tampon 12 has been inserted for use. Prior to use, the set of protrusions 37 of the barrel 20 threadedly engages with the annular ridge 47 of the plunger 40 such that the barrel 20 and the plunger 40 are securely attached. When the applicator 10 is first used, the cap 60 is removed, and optionally, the user may remove the lid 56 of the storage compartment 54 of the plunger 40, and retrieve the tampon 12 for use. The user then slides the barrel 20 to the first position of FIG. 2 to allow insertion of the digital tampon 12. In some embodiments, the tampon applicator 10 may click for tactile feedback in the first position. As shown in FIG. 2, once the barrel 20 has been moved to this first position relative to the plunger 40, the inner chamber 32 may be loaded with the tampon 12 through the window 34 formed on the outer surface 30 of the barrel 20. In this embodiment, the window 34 is formed in a similar shape as the tampon 12, but in other embodiments, the window 34 may be rectangular, oval, or any other shaped deemed suitable by those skilled in the art.

FIG. 3 is a perspective view illustrating the tampon applicator 10 of FIG. 2 once the tampon applicator 10 has been moved to a second position, thereby dispensing the tampon 12. As shown in FIG. 3, a user may slide the barrel 20 of the applicator 10 toward the base 48 of the plunger 40 to dispense the tampon 12 out of the upper opening of the barrel 20, and to close the applicator 10. A user may wish to use the cap 60 in this configuration.

The grip portion 36 of the barrel 20 and the flat lid 56 of the plunger 40 aid in all telescopic movements of the applicator 10, each providing a visual tactile cue to the user for ideal hand positioning. The plunger 40 and/or barrel 20 may be shaped or textured to cause tactile feedback (e.g., clicking sensation) when the applicator 10 is fully opened or closed. During use, the inner ring 38 of the barrel 20 may also click to secure to the top ring 50 of the base 48 of the plunger 40.

As used in this application, the words "a," "an," and "one" are defined to include one or more of the referenced item unless specifically stated otherwise. The terms "approximately" and "about" are defined to mean +/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by claims made to the invention.

What is claimed is:

1. A tampon applicator for dispensing a tampon, the tampon applicator comprising:
    a barrel extending from a proximal end to a distal end, the distal end having a base opening, and the proximal end having an upper opening exposing an inner chamber;
    a window formed in similar shape as the tampon, the window being formed in the barrel shaped to receive the tampon into the inner chamber, the window not extending to the base opening in the distal end of the barrel, so that the distal end of the barrel has a tubular construction;
    a set of protrusions extending inwardly from the inner chamber proximate the distal end of the barrel;
    an inner ring of the inner chamber proximate the distal end of the barrel;
    a plunger extending from a first end to a second end, the first end having a base;
    a top ring on the base of the plunger, wherein the inner ring of the barrel is adapted to removably snap into the top ring; and
    an annular ridge on the second end of the plunger, the annular ridge having a threaded shape for threaded engagement with the set of protrusions of the barrel, so that the annular ridge can be moved through the set of protrusions by rotating the plunger relative to the barrel, the annular ridge preventing the plunger from being retracted from the barrel absent a rotation of the plunger relative to the barrel.

2. The tampon applicator of claim 1, wherein the set of protrusions of the barrel include four approximately equidistant protrusions.

3. The tampon applicator of claim 1, wherein the upper opening of the barrel tapers at least partway down either side of the barrel.

4. The tampon applicator of claim 1, wherein the base of the plunger includes a lower opening that exposes a storage compartment, the lower opening further having a removable lid.

5. The tampon applicator of claim 1, further including a cap that snaps into the base of the plunger to cover both the barrel and the plunger when the plunger is positioned within the barrel.

* * * * *